United States Patent
Kimata et al.

(10) Patent No.: US 10,866,210 B2
(45) Date of Patent: Dec. 15, 2020

(54) GAS SENSOR

(71) Applicant: DENSO CORPORATION, Kariya (JP)

(72) Inventors: Takehito Kimata, Kariya (JP);
Yuusuke Toudou, Kariya (JP);
Yuusuke Kawamoto, Kariya (JP)

(73) Assignee: DENSO CORPORATION, Kariya (JP)

( * ) Notice: Subject to any disclaimer, the term of this patent is extended or adjusted under 35 U.S.C. 154(b) by 385 days.

(21) Appl. No.: 15/550,469

(22) PCT Filed: Feb. 12, 2016

(86) PCT No.: PCT/JP2016/054082
§ 371 (c)(1),
(2) Date: Aug. 11, 2017

(87) PCT Pub. No.: WO2016/129661
PCT Pub. Date: Aug. 18, 2016

(65) Prior Publication Data
US 2018/0031518 A1 Feb. 1, 2018

(30) Foreign Application Priority Data
Feb. 12, 2015 (JP) .................. 2015-025775
Jan. 11, 2016 (JP) .................. 2016-003130

(51) Int. Cl.
*G01N 27/416* (2006.01)
*G01N 27/41* (2006.01)
(Continued)

(52) U.S. Cl.
CPC ......... *G01N 27/416* (2013.01); *G01N 27/409* (2013.01); *G01N 27/4067* (2013.01);
(Continued)

(58) Field of Classification Search
CPC .................. G01N 27/4067; G01M 15/104
See application file for complete search history.

(56) References Cited

U.S. PATENT DOCUMENTS 4,883,947 A * 11/1989 Murase .............. G01N 27/4067
219/553
5,236,569 A * 8/1993 Murase ................ G01N 27/417
204/410

(Continued)

FOREIGN PATENT DOCUMENTS

JP 2010-271283 12/2010
JP 2011-099712 5/2011

OTHER PUBLICATIONS

International Search Report dated May 10, 2016, issued in Application No. PCT/JP2016/054082 (2 pages).

*Primary Examiner* — Sadie White
(74) *Attorney, Agent, or Firm* — Nixon & Vanderhye PC

(57) ABSTRACT

A gas sensor is equipped with a solid electrolyte body, a pump electrode, a sensor electrode, and a heater. In the gas sensor, a region of the whole of a front end portion of a heater base in which a heating element is disposed is broken down into three regions: an intermediate region defined between a front end and a base end of the sensor electrode, a front end region located closer to a front end side than the intermediate region is, and a base end region located closer to a base end side than the intermediate region is. A resistance value per unit area of a heating element lying in the base end region and a resistance value per unit area of the heating element lying in the front end region is selected to be higher than that of the heating element lying in the intermediate region, thereby keeping the temperature of a region around the sensor electrode at a desired level even when the temperature of gas changes.

12 Claims, 6 Drawing Sheets

(51) Int. Cl.
 G01N 27/409 (2006.01)
 G01N 27/417 (2006.01)
 G01N 27/406 (2006.01)
 G01N 27/419 (2006.01)
 G01M 15/10 (2006.01)
 G01N 33/00 (2006.01)

(52) U.S. Cl.
 CPC ........... G01N 27/41 (2013.01); G01N 27/419 (2013.01); G01N 27/4175 (2013.01); G01M 15/104 (2013.01); G01M 15/106 (2013.01); G01N 33/0016 (2013.01)

(56) References Cited

U.S. PATENT DOCUMENTS

| | | |
|---|---|---|
| 6,287,439 B1 | 9/2001 | Kato et al. |
| 6,861,939 B1 * | 3/2005 | Bischof .............. G01N 27/4067 219/482 |
| 2009/0250344 A1 | 10/2009 | Ohya et al. |
| 2016/0209354 A1 | 7/2016 | Araki et al. |
| 2016/0209358 A1 | 7/2016 | Toudou et al. |

* cited by examiner

GAS SENSOR

CROSS-REFERENCE TO RELATED APPLICATION

This application is the U.S. national phase of International Application No. PCT/JP2016/054082 filed Feb. 12, 2016 which designated the U.S. and claims priority to JP Patent Application Nos. 2015-025775 filed Feb. 12, 2015 and 2016-003130 filed Jan. 11, 2016, the entire contents of each of which are hereby incorporated by reference.

TECHNICAL FIELD

The present invention generally relates to a gas sensor which measures the concentration of a given gas component contained in oxygen-containing gas.

BACKGROUND ART

Gas sensors which are designed to have a plate-like heater stacked on a plate-like solid electrolyte body are equipped with a plurality of types of cells through which electric current flows by means of a portion of the solid electrolyte body and a pair of electrodes disposed on the portion of the solid electrolyte body. The cells are heated by a heater up to a suitable temperature at which the electrodes have catalytic activity.

For example, a gas sensor, as taught in patent literature 1, has electrodes disposed on a solid electrolyte body to form a first pumping cell and a second pumping cell and also has a heater stacked on the solid electrolyte body. The first pumping cell works to control the oxygen partial pressure. The second pumping cell works to measure a given gas component contained in measurement gas. The heater works to heat the first pumping cell and the second pumping cell. A resistance value of a resistance portion of the heater which faces the first pumping cell is selected to be higher than that of a resistance portion of the heater which faces the second pumping cell. This decreases the temperature of the second pumping cell to eliminate a change in offset current which will be detected when the concentration of the given gas component is zero.

PRIOR ART DOCUMENT

Patent Literature

PATENT LITERATURE 1 Japanese patent first publication No. 2009-265085

SUMMARY OF THE INVENTION

Problem to be Solved by the Invention

The gas sensor is, however, retained by a housing through an insulator, so that heat will be dissipated or transferred from the gas sensor to the insulator. Such heat dissipation will result in considerable adverse effects on the gas sensor which are usually changed with a change in temperature of the gas. Techniques for minimizing a change in temperature of each cell (i.e., each electrode) of the gas sensor when the temperature of the gas changes are required.

The invention was made in view of the above problem. It is an object of the invention to provide a gas sensor which is capable of keeping the temperature of a region around a sensor electrode at a desired value when the temperature of gas changes.

Means for Solving the Problem

According to one aspect of the invention, there is provided a gas sensor which comprises: (a) a plate-like solid electrolyte body (2) which has oxygen ion conductivity; (b) a pump electrode (21) which is disposed on a first surface (201) of the solid electrolyte body which is exposed to gas (G) containing oxygen, the pump electrode being used to regulate an oxygen concentration in the gas; (c) a sensor electrode (22) which is disposed closer to a base end side than the pump electrode is on the first surface of the solid electrolyte body, the sensor electrode being used to measure a concentration of a given gas component of the gas whose oxygen concentration has already been regulated by the pump electrode; and (d) a plate-like heater (3) which is arranged to face the solid electrolyte body and works to heat the solid electrolyte body.

The gas sensor has a front end side in a lengthwise direction (L) thereof which is exposed to the gas and also has a base end side in the lengthwise direction which is retained by an insulator (6).

The heater is made up of a heater base (31) and a conductive layer (32) disposed in the heater base.

The conductive layer includes a pair of leads (40) arranged on the base end side and a heating element (4). The heating element is arranged closer to the front end side than the leads are, connected to the leads, and smaller in sectional area than that of the leads.

An entire region (R) of a front end portion (11) of the heater base in which the heating element is installed is broken down into three regions: a base end region (R1), an intermediate region (R2), and a front end region (R3) which are arranged in the above lengthwise direction. The intermediate region (R2) is located between a front end (222) and a base end (221) of the sensor electrode. The front end region (R3) is located closer to the front end side than the intermediate region is. The base end region (R1) is located closer to the base end side than the intermediate region is. Resistance values per unit area of the heating element in the base end region and the front end region are higher than that in the intermediate region.

Beneficial Effects

In the above gas sensor, how to form the heating element of the conductive layer of the heater is designed.

Specifically, when the region of the whole of the front end portion of the heater base of the heater in which the heating element is arranged is broken down into three regions: the intermediate region, the front end region, and the base end region, the resistance value per unit area of the heating element in the base end region is higher than that in the intermediate region. This enables a portion of the solid electrolyte body which is opposed to the base end region located closest to the insulator to be heated more strongly than a portion of the solid electrolyte body which is opposed to the intermediate region and a region around the sensor electrode.

The strong heating of the portion of the solid electrolyte body close to the insulator minimizes a risk that the sensor electrode is adversely affected by the dissipation or transfer of heat to the base end side where the insulator is disposed when the temperature of the gas is low or being dropping.

The resistance value per unit area of the heating element lying in the front end region is selected to be higher than that of the heating element lying in the intermediate region. This enables a portion of the solid electrolyte body which is opposed to the front end region and a region around the pump electrode to be heated more strongly than the portion of the solid electrolyte body which is opposed to the intermediate region and the region around the sensor electrode, thereby facilitating the ease with which the temperature of a region around the pump electrode is brought to a desired temperature which provides catalytic activity.

It is, therefore, possible for the gas sensor to keep the temperature of the region around the sensor electrode at a suitable level when the temperature of the gas changes. This ensures a high accuracy in measuring the concentration of the given gas component using the sensor electrode.

EMBODIMENT FOR CARRYING OUT THE INVENTION

Figure 1:
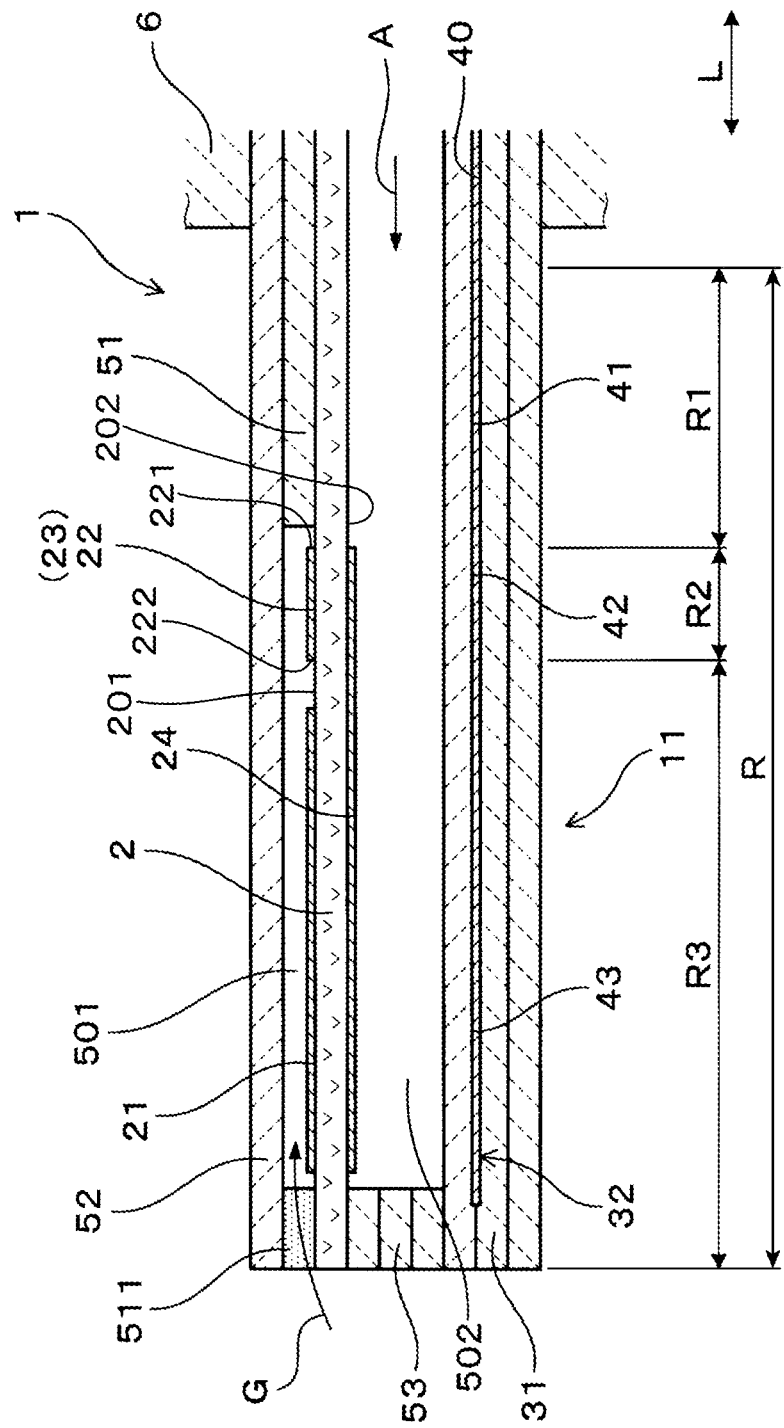
FIG. 1 is a sectional view which illustrates a gas sensor according to the first embodiment.

Preferred embodiments of the above described gas sensor will be discussed below.

"A resistance value per unit area", as referred to in this disclosure, represents a value derived by dividing a resistance value of a heating element lying in each of a plurality of regions of the gas sensor by an area of a corresponding one of the regions. "The resistance value" represents a value derived by measuring an electrical current flowing through the heating element when a given voltage is applied to the heating element lying in each of the regions and dividing the given voltage by the measured electrical current.

An intermediate region represents a region of the heater base which is located between a front end of a sensor electrode and a base end of the sensor electrode which is opposed to the front end. A front end region represents the whole of a region of the heater base which is closer to the front end side of the heater base than the front end of the sensor electrode is. A base end region represents the whole of a region of a front end portion of the heater base which is located closer to the base end side of the heater base than the base end of the sensor electrode is. The front end portion has the heating element disposed therein. The front end portion of the heater base occupies the whole of a region of the heater base which is located closer to the front end side than an end of the heater base to which leads are joined.

The whole of the heating element has a constant sectional area defined in a widthwise direction of the heating element. A length per unit area of the heating element arranged in the base end region and a length per unit area of the heating element arranged in the front end region may be increased to be greater than a length per unit area of the heating element lying in the intermediate region.

The increased length of the heating element lying in the base end region results in an increased resistance value per unit area of the heating element in the base end region which is higher than the resistance value per unit area of the heating element lying in the intermediate region. Similarly, the increased length of the heating element lying in the front end region results in an increased resistance value per unit area of the heating element in the front end region which is higher than the resistance value per unit area of the heating element lying in the intermediate region.

"The length per unit area" represents a value derived by dividing an entire length of a portion of the heating element lying in each region by an area of that region.

An average value of a transverse sectional area per unit length of the heating element lying in the base end region and an average value of a transverse sectional area per unit length of the heating element lying in the front end region may be decreased to be smaller than an average value of a transverse sectional area per unit length of the heating element lying in the intermediate region.

The decreased sectional area of the heating element lying in the base end region results in an increased resistance value per unit area of the heating element in the base end region which is higher than the resistance value per unit area of the heating element lying in the intermediate region. Similarly, the decreased sectional area of the heating element lying in the front end region results in an increased resistance value per unit area of the heating element in the front end region which is higher than the resistance value per unit area of the heating element lying in the intermediate region.

"The average value of the sectional area per unit area" represents a value derived by dividing an average value of a transverse sectional area, as defined in the widthwise direction, of the heating element lying in each region by an area of that region. "The constant sectional area of the heating element" may include an error of ±10% thereof.

Embodiment

A gas sensor according to embodiments will be described below with reference to the drawings.

First Embodiment

Figure 2:
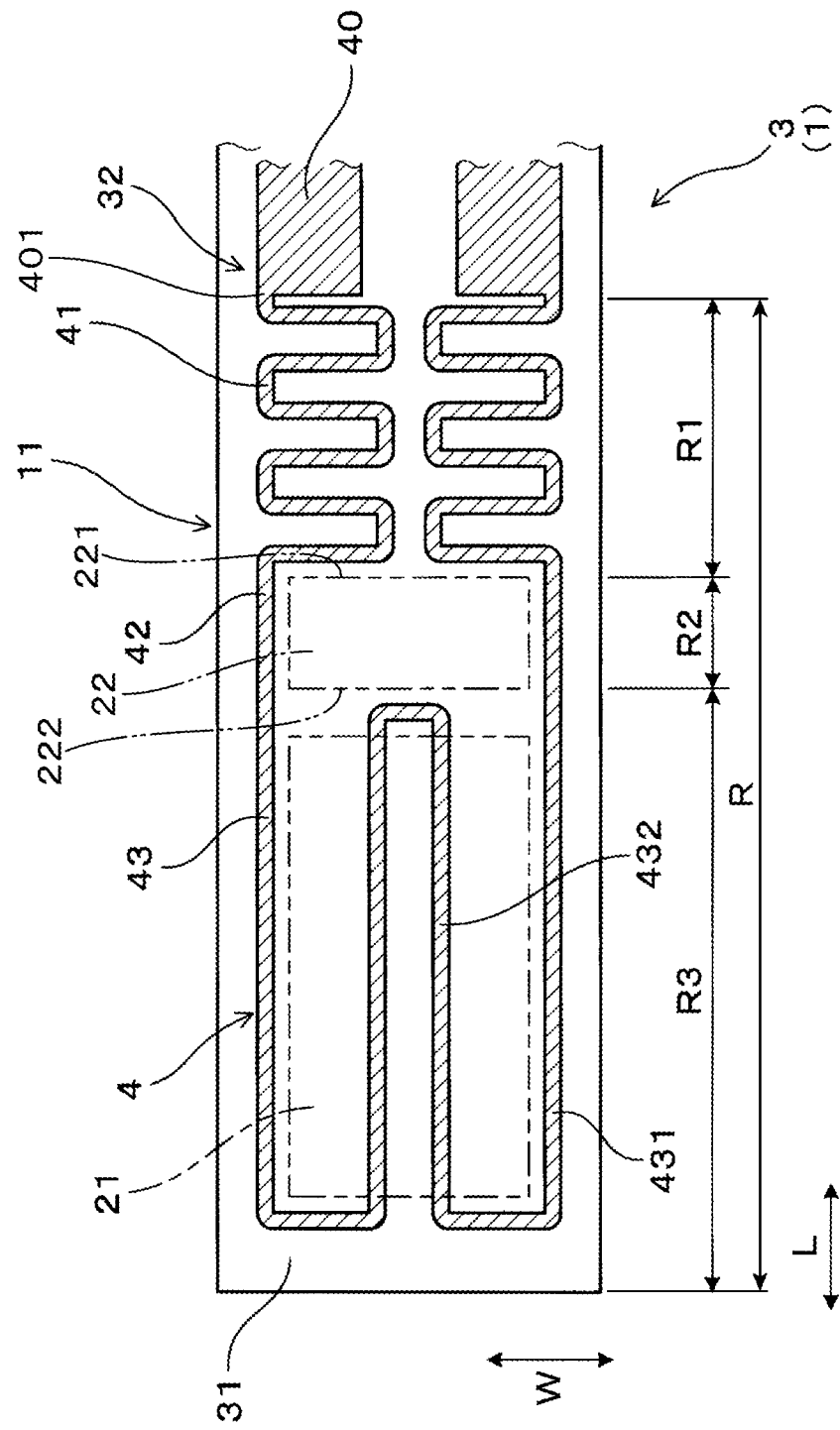
FIG. 2 is a plan view which illustrates the layout of a heating element in a heater base of a gas sensor according to the first embodiment.

The gas sensor 1 is, as illustrated in FIGS. 1 and 2, equipped with the solid electrolyte body 2, the pump electrode 21, the sensor electrode 22, and the heater 3.

The solid electrolyte body 2 has oxygen ion conductivity and is shaped in the form of a plate. The pump electrode 21 is disposed on the first surface 201 of the solid electrolyte body 2 which is exposed to the gas G containing oxygen. The pump electrode 21 is used to regulate the oxygen concentration of the gas G. The sensor electrode 22 is disposed on the first surface 201 of the solid electrolyte body 2 closer to a base end side of the solid electrolyte body 2 than the pump electrode 21 is. The sensor electrode 22 is used to measure the concentration of the given gas component in the gas G whose oxygen concentration has already been regulated by the pump electrode 21. The heater 3 is shaped in the form of a plate and faces the solid electrolyte body 2 to heat the solid electrolyte body 2 and the electrodes 21 and 22.

The gas sensor 1 has a given length with two ends opposed to each other in the lengthwise direction thereof. In this disclosure, one of the ends of the gas sensor 1 which is exposed to the gas G will be referred to as a front end side, while the other end retained by the insulator 6 will also be referred to as a base end side. The gas sensor 1 is, as described above, shaped to be long. The front end side of the gas sensor 1 is also a free end. The base end side of the gas sensor 1 is, as described above, opposed to the front end side in the lengthwise direction L and held by the insulator 6.

The heater 3 is, as illustrated in FIGS. 1 and 2, made up of insulating heater bases 31 and the conductive layer 32 disposed between the heater bases 31. The conductive layer 32 includes a pair of leads 40 arranged on the base end side thereof and the heating element 4 which is located closer to the front end side than the leads 40 are. The heating element 4 connects the leads 40 together and is smaller in transverse sectional area than the leads 40.

The heater bases 31 of the gas sensor 1, as illustrated in FIG. 2, have a portion in which the heating element 4 is disposed near the front end of the gas sensor 1. In the following discussion, such a portion will be referred to as a front end portion 11. An entire region of the front end portion 11 will be referred to as a region R which is, as can be seen from the drawing, broken down into three regions: a region R1, a region R2, and a region R3 which are arranged in the lengthwise direction L. The region R2 lies between the front end 222 of the sensor electrode 22 and the base end 221 of the sensor electrode 22 and will also be referred to below as an intermediate region R2. The region R3 is located closer to the front end side than the intermediate region R2 is and will also be referred to below as a front end region R3. The region R1 is closer to the base end side than the intermediate region R2 is and will also be referred to below as a base end region R1. The pattern or layout of the heating element 4 is selected to have resistance values per unit area of the heating element 41 in the base end region R1 and the heating element 43 in the front end region R3 which are higher than that of the heating element 42 in the intermediate region R2. In other words, the heating element 4 is made up of three sections 41, 42, and 43. The section 41 lies in the region R1. The section 42 lies in the region R2. The section 43 lies in the region R3. The resistance value per unit area is expressed by a value derived by dividing a value of resistance of each of the heating elements 41, 42, and 43 arranged in the regions R1, R2, and R3 by an area of a corresponding one of the regions R1, R2, and R3. The front end portion 11 of the heater bases 31 in which the heating element 4 is disposed occupies the whole of the region R which is located closer to the front end side than the ends 401 of the heating element 4 joined to the leads 40 in the heater bases 31 is.

The gas sensor 1 will be described in detail with reference to FIGS. 1 to 3.

In use, the gas sensor 1 is installed in an exhaust pipe of an internal combustion engine. The gas G contains oxygen and is exhaust gas flowing through the exhaust pipe extending from the internal combustion engine. The given gas component is NOx (nitrogen oxide) contained in the exhaust gas. The gas sensor 1 is retained by a housing using the insulator 6. The housing is secured to the exhaust pipe. The gas sensor 1 has a front end portion extending outside the insulator 6. The front end portion is covered with a protective cover with gas holes through which the gas G passes.

The solid electrolyte body 2, as illustrated in FIG. 1, has the first surface 201 and the second surface 202 which are opposed to each other in a thickness-wise direction of the solid electrolyte body 2. The reference electrode 24 is disposed on the second surface 202 exposed to atmospheric air as a reference gas A. The reference electrode 24 is arranged on a portion of the second surface 202 which coincides or overlaps with the pump electrode 21 and the sensor electrode 22 disposed on the first surface 201 of the solid electrolyte body 2 in the thickness-wise direction of the solid electrolyte body 2. The reference electrode 24 may be made of a single electrode whose size fully overlap with the pump electrode 21 and the sensor electrode 22. The reference electrode 24 may alternatively be made of a combination of a plurality of discrete electrodes or two electrodes one for each of the pump electrode 21 and the sensor electrode 22.

The pump electrode 21, the sensor electrode 22, and the reference electrode 24 are provided on the single solid electrolyte body 2. The plate-like insulator 52 is stacked on the first surface 201 of the solid electrolyte body 2 through the spacer 51. The gas chamber 501 into which the gas G is introduced is formed by the solid electrolyte body 2, the spacer 51, and the insulator 52 on the first surface 201 of the solid electrolyte body 2. The diffusion resistance layer 511 through which the gas G is introduced into the gas chamber 501 while being subjected to a given diffusion resistance is disposed in a hole formed in the spacer 51. The heater 3 is stacked on the second surface 202 of the solid electrolyte body 2 through the spacer 53. The reference gas chamber 502 into which the reference gas A is introduced is formed by the solid electrolyte body 2, the spacer 53, and the heater 3 on the second surface 202 of the solid electrolyte body 2.

The pump electrode 21 and the reference electrode 24 are made from material, such as platinum or gold, which is catalytically active against oxygen. The sensor electrode 22 is made of material in which rhodium which is catalytically active against NOx is added to platinum.

In the gas sensor 1, a pump cell is formed by the pump electrode 21, the reference electrode 24 (i.e. a portion of the reference electrode 24 in this embodiment), and a portion of the solid electrolyte body 2 interposed between the pump electrode 21 and the reference electrode 24. The pump cell is engineered to apply voltage between the pump electrode 21 and the reference electrode 24 to create a flow of oxygen ion current between the pump electrode 21 and the reference electrode 24, thereby removing oxygen from the gas G.

In the gas sensor 1, sensor cell is formed by the sensor electrode 22, the reference electrode 24 (i.e., a portion of the reference electrode 24 in this embodiment), and a portion of the solid electrolyte body 2 interposed between the sensor electrode 22 and the reference electrode 24. The sensor cell is engineered to measure the oxygen ion current flowing between the sensor electrode 22 and the reference electrode 24 when the voltage is being applied between the sensor electrode 22 and the reference electrode 24 for calculating the concentration of NOx contained in the gas G as a function of a level of the oxygen ion current.

The heater bases 31, the insulator 52, and the spacers 51 and 53 are made of ceramic such as alumina. The conductive layer 32 is made of conductive material which has a constant thickness and is disposed in the heater base 31. The conductive layer 32 is firmly held between the two heater bases 31. The two leads 40 of the conductive layer 32 extend parallel to each other in a base end portion of the heater bases 31. The heating element 4 of the conductive layer 32 is smaller in transverse sectional area than the leads 40, thereby causing the heating element 4 to generate a greater amount of Joule heat than the leads 40 when the electrical current is delivered to the leads 40.

The heating element 4, as illustrated in FIG. 2, has a constant width over the whole of length thereof. Additionally, the heating element 4 also has a constant transverse sectional area over the whole of length thereof. The patter or layout of the heating element 4 changes among the base end region R1, the intermediate region R2, and the front end region R3. The change in layout of the heating element 4 results in a difference in length per unit area among the heating elements 41, 42, and 43 in the regions R1, R2, and R3. The length per unit area, as referred to herein, is derived by dividing an overall length of each of the heating elements 41, 42, and 43 disposed in the regions R1, R2, and R3 by an area of a corresponding one of the regions R1, R2, and R3.

Specifically, the length per unit area of the heating element 41 in the base end region R1 and the length per unit area of the heating element 43 in the front end region R3 are greater than that of the heating element 42 in the intermediate region R2. The length per unit area of the heating element 41 in the base end region R1 is greater than that of the heating element 43 in the front end region R3.

The heating element 41 in the base end region R1 is made up of portions extending parallel in the lengthwise direction L of the heater 3 and portions extending parallel in the widthwise direction W perpendicular to the lengthwise direction L and meanders in the widthwise direction W. The heating element 41 in the base end region R1 is made up of two conductors which extend symmetrically in the widthwise direction W. The heating element 42 in the intermediate region R2 is made up of two conductors which extend parallel in the lengthwise direction L and symmetrically in the widthwise direction W. The conductors of the heating element 42 lie outside a portion of the intermediate region R2 in the widthwise direction W which coincides or overlaps with the sensor electrode 22 in the thickness-wise direction of the heater base 31. The heating element 43 in the front end region R3 is made up of portions extending parallel in the lengthwise direction L and portions extending parallel in the widthwise direction and meanders in the lengthwise direction L. In other words, the heating element 43 in the front end region R3 is made up of two conductors which are symmetrical in the widthwise direction W. The heating element 43 in the front end region R3 includes two outside portions 431 extending parallel in the lengthwise direction L and two inside portions 432 extending parallel in the lengthwise direction L which are joined together on the front end side. The inside portions 432 are joined together at the base end side.

The gas sensor 1, as described above, has the entire region R of the front end portion 11 of the heater bases 31 in which the heating element 4 is disposed. The entire region R is classified into three regions arranged in the lengthwise direction L of the gas sensor 1. The calorific properties of the heating element 4 (i.e., the amount of heat generated by the heating element 4) are different among the three regions which are the front end region R3 opposed to the pump electrode 21, the intermediate region R2 lying between the front end 222 and the base end 221 of the sensor electrode 22, and the base end region R1 located closer to the base end side than the sensor electrode 22 is.

The resistance values per unit area of the heating element 41 in the base end region R1 and the heating element 43 in the front end region R3 are selected to be higher than that of the heating element 42 in the intermediate region R2, thereby increasing the amount of heat generated in the base end region R1 and the front end region R3 to be greater than that in the intermediate region R2.

The above structure is capable of heating a portion of the solid electrolyte body 2 which is opposed in the thickness-wise direction of the heater bases 31 to the base end region R1 which is the closest to the insulator 6 among the three regions R1 to R3 more strongly than a portion of the solid electrolyte body 2 which is opposed to the intermediate region R2 and a region around the sensor electrode 22.

The resistance value per unit area of either of the heating element 41 in the base end region R1 or the heating element 43 in the front end region R3 may be selected to be higher.

The front end region R3 is less subjected to the dissipation of heat (i.e., transfer of heat) to the base end side where the insulator 6 is disposed, so that a region around the pump electrode 21 facing the front end region R3 will be the highest in temperature in the lengthwise direction L of the gas sensor 1. Conversely, the base end region R1 is highly subjected to the dissipation of heat to the base end side where the insulator 6 is disposed. For these reasons, the gas sensor 1 is designed to have the resistance value per unit area of the heating element 41 in the base end region R1 which is higher than that of the heating element 43 in the front end region R3, thereby causing the portion of the solid electrolyte body 2 opposed to the base end region R1 to be more strongly heated. The region around the sensor electrode 22 opposed to the intermediate region R2 and a portion closer to the base end side than the sensor electrode 22 is, therefore, kept a desired temperature lower than that of a region around the pump electrode 21. The temperature of the region around the pump electrode 21 is kept at a temperature suitable for exhibiting the catalytic activity.

Usually, the temperature of the gas G (i.e., the exhaust gas) emitted from the internal combustion engine is lower than a target temperature at which the heater 3 heats the solid electrolyte body 2. The gas G (i.e., the exhaust gas) may be greatly lower than the target temperature at which the solid electrolyte body 2 is heated when the internal combustion engine is being lean-burned. This gives rise to a problem about the dissipation or transfer of heat from the gas sensor 1 to the base end side where the insulator 6 lies.

The temperature of the gas G (i.e., the exhaust gas) flowing through the exhaust pipe of the internal combustion engine in which the gas sensor 1 is installed usually rises and drops cyclically in response to combustion cycles in the internal combustion engine. When the temperature of the gas G drops, the problem regarding the dissipation or transfer of heat from the gas sensor 1 to the base end side on which the insulator 6 lies will be developed.

For the reasons as described above, the gas sensor 1 is designed to strongly heat the solid electrolyte body 2 near the insulator 6 to minimize the adverse effects on the sensor electrode 22 which arises from the dissipation or transfer of heat to the base end side where the insulator 6 lies when the temperature of the gas G drops.

The gas sensor 1, therefore, works to keep the temperature around the sensor electrode 22 at a desired level even when the temperature of the gas G changes, thereby ensuring the stability of accuracy in measuring the concentration of the given gas component using the sensor electrode 22.

Figure 3:
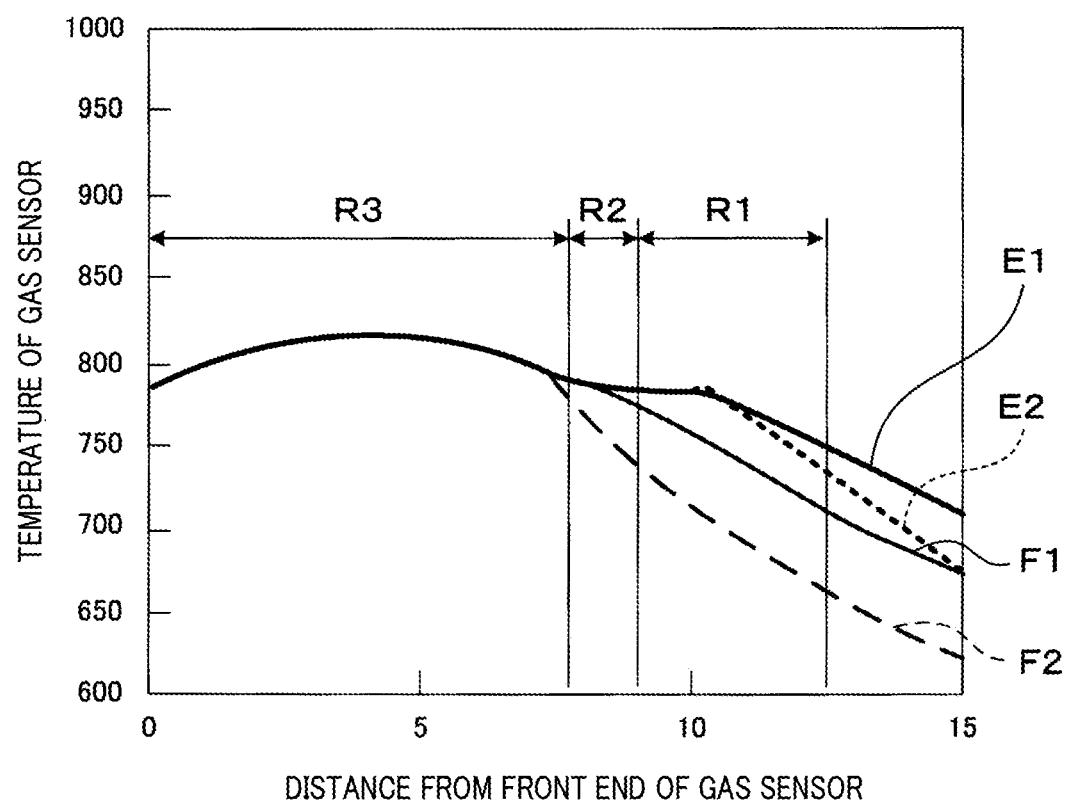
FIG. 3 is a graph which represents a relation between a distance from a front end of a gas sensor and a corresponding temperature of the gas sensor according to the first embodiment.
Figure 9:
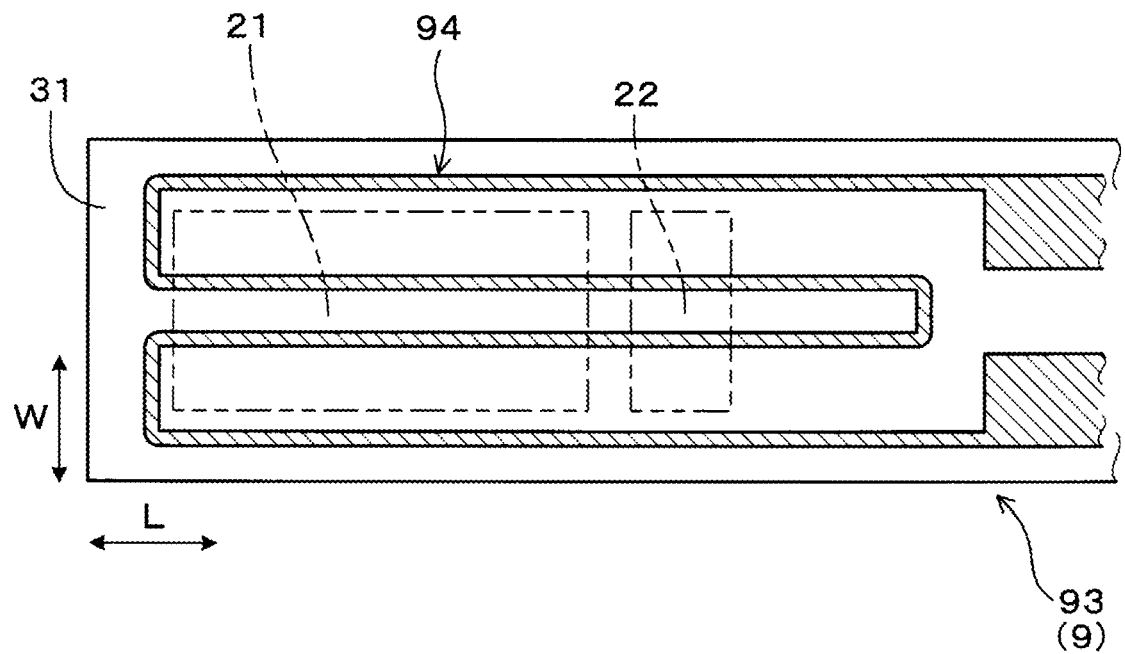
FIG. 9 is a plan view which shows the layout of a heating element in a heater base of a comparative example of a gas sensor.

FIG. 3 demonstrates a relation between the distance (mm) from the front end of the gas sensor 1 and the temperature of a portion of the gas sensor 1 located at a corresponding distance from the front end of the gas sensor 1 in FIG. 2. FIG. 3 also demonstrates such a relation of a comparative example of a conventional gas sensor 9 in FIG. 9. The conventional gas sensor 9 is, as illustrated in FIG. 9, equipped with the heater 93. The heating element 94 of the heater 93 does not have the heating element 41 in the base end region R1 of the heater bases 31. The graph of FIG. 3 represents results of simulations about the temperature of the gas sensors 1 and 9.

In FIG. 3, a change in temperature of the gas sensor 1 when the temperature of the gas G is 500° C. is represented by "E1". A change in temperature of the gas sensor 1 when the temperature of the gas G is 200° C. is represented by "E2". A change in temperature of the gas sensor 9 when the temperature of the gas G is 500° C. is represented by "F1". A change in temperature of the gas sensor 9 when the temperature of the gas G is 200° C. is represented by "F2".

In either of the gas sensor 1 of this embodiment or the conventional gas sensor 9, the temperature around the center of the pump electrode 21 (i.e., the pump cell) in the lengthwise direction L has a peak. The temperature around the sensor electrode 22 (i.e., the sensor cell) is lower than that around the pump electrode 21.

In the conventional gas sensor 9, when the temperature of the gas G decreases from 500° C. to 200° C., the temperature around the sensor electrode 22 greatly drops. Such a drop is caused by the dissipation or transfer of heat to the base end of the gas sensor 9.

In the gas sensor 1 of this embodiment, when the temperature of the gas G drops from 500° C. to 200° C., the temperature around the sensor electrode 22 hardly changes. Such beneficial effects to minimize a change in temperature around the sensor electrode 22 are obtained by heating the portion of the solid electrolyte body 6 opposed to the base end region R1 closest to the insulator 6 more strongly than the portion of the solid electrolyte body 2 opposed to the intermediate region R2 and the region around the sensor electrode 22. The gas sensor 1 serves to keep the temperature around the sensor electrode 22 at a desired level even when the temperature of the gas G changes.

In the case where the gas sensor 1 is equipped with a monitor electrode 23 (i.e., a monitor cell) which will be described later in the second embodiment, the temperature of the monitor cell 23 will be identical with that of the sensor electrode 22.

Second Embodiment

This embodiment is an example (see FIG. 1) where the monitor electrode 23 is arranged adjacent to the sensor electrode 22 in the widthwise direction W and located closer to the base end side than the pump electrode 21 is on the first surface 201 of the solid electrolyte body 2.

The monitor electrode 23 is used to measure the oxygen concentration of the gas G whose oxygen concentration has already been regulated by the pump electrode 21. The distance between the center of the pump electrode 21 and the center of the sensor electrode 22 is substantially identical with that between the center of the pump electrode 21 and the center of the monitor electrode 23.

The monitor electrode 23 is made from material, such as platinum or gold, which is catalytically active against oxygen. The reference electrode 24 is disposed on the second surface 202 of the solid electrolyte body 2 and faces the monitor electrode 23 in the thickness-wise direction of the solid electrolyte body 2. The gas sensor 1 has a monitor cell defined by the monitor electrode 23, the reference electrode 24 (i.e., a portion of the reference electrode 24 in this embodiment), and a portion of the solid electrolyte body 2 interposed between the monitor electrode 23 and the reference electrode 24. The monitor cell is engineered to measure an oxygen ion current flowing between the monitor electrode 23 and the reference electrode 24 when voltage is being applied between the monitor electrode 23 and the reference electrode 24.

The sensor cell develops a flow of oxygen ion current resulting from NOx and residual oxygen. The monitor cell develops a flow of oxygen ion current resulting from the residual oxygen. The concentration of NOx contained in the gas G is, therefore, derived by subtracting a value of the oxygen ion current in the monitor cell from that of the oxygen ion current in the sensor cell.

The pump electrode 21, the sensor electrode 22, the monitor electrode 23, and the reference electrode 24 are formed by the single solid electrolyte body 2.

The other arrangements of the gas sensor 1 of this embodiment are identical with those in the first embodiment. The same reference numbers as employed in the first embodiment will refer to the same parts. The same beneficial effects as those in the first embodiment are provided.

Third Embodiment

Figure 4:
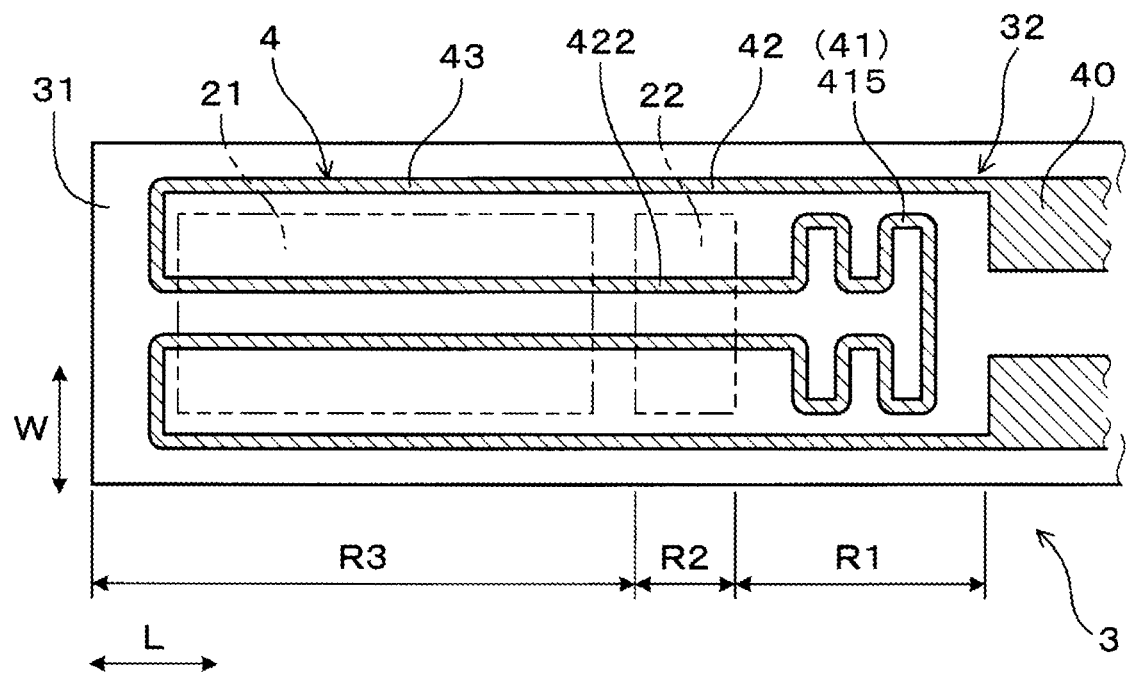
FIG. 4 is a plan view which illustrates the layout of a heating element in a heater base of a gas sensor according to the third embodiment.

This embodiment is different in layout of the heating element 4 in the heater bases 31 from the first embodiment. The heating element 4 in the base end region R1, as illustrated in FIG. 4, has the central portion 415 extending from the inner portion 422 of the heating element 42 in the intermediate region R2. The volume of the heating element 42 in the intermediate region R2 is greater than that in the first embodiment, thereby enabling the region around the sensor electrode 22 to be heated strongly as compared with the first embodiment.

Figure 5:
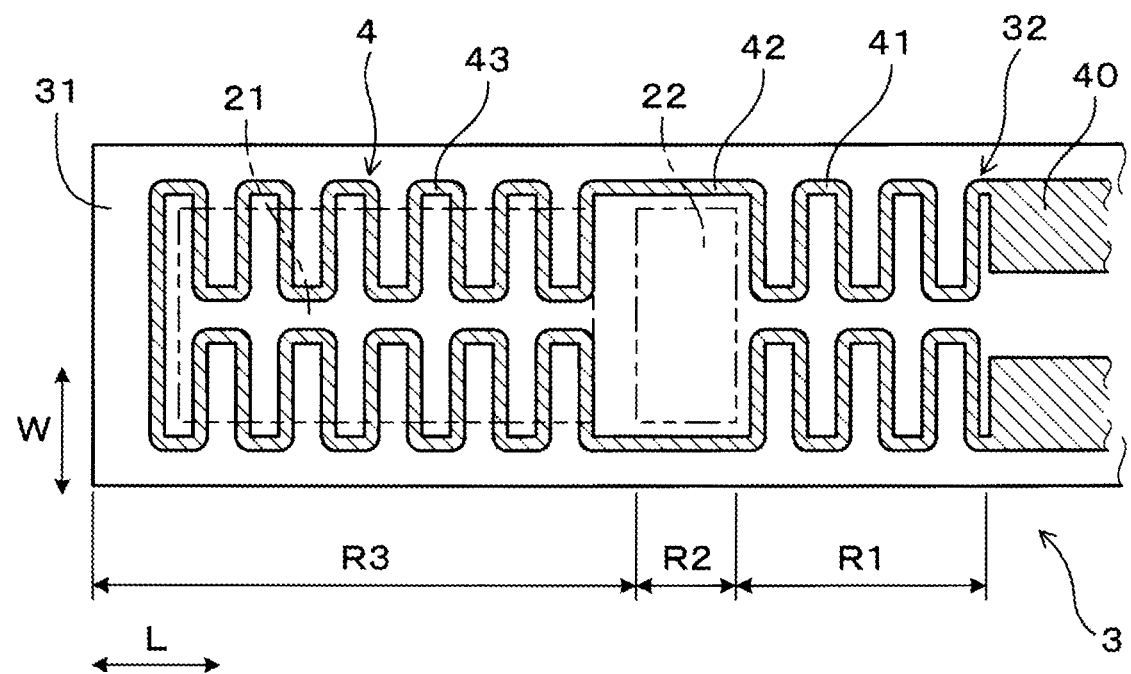
FIG. 5 is a plan view which illustrates the layout of a heating element in a heater base of another gas sensor according to the third embodiment.
Figure 6:
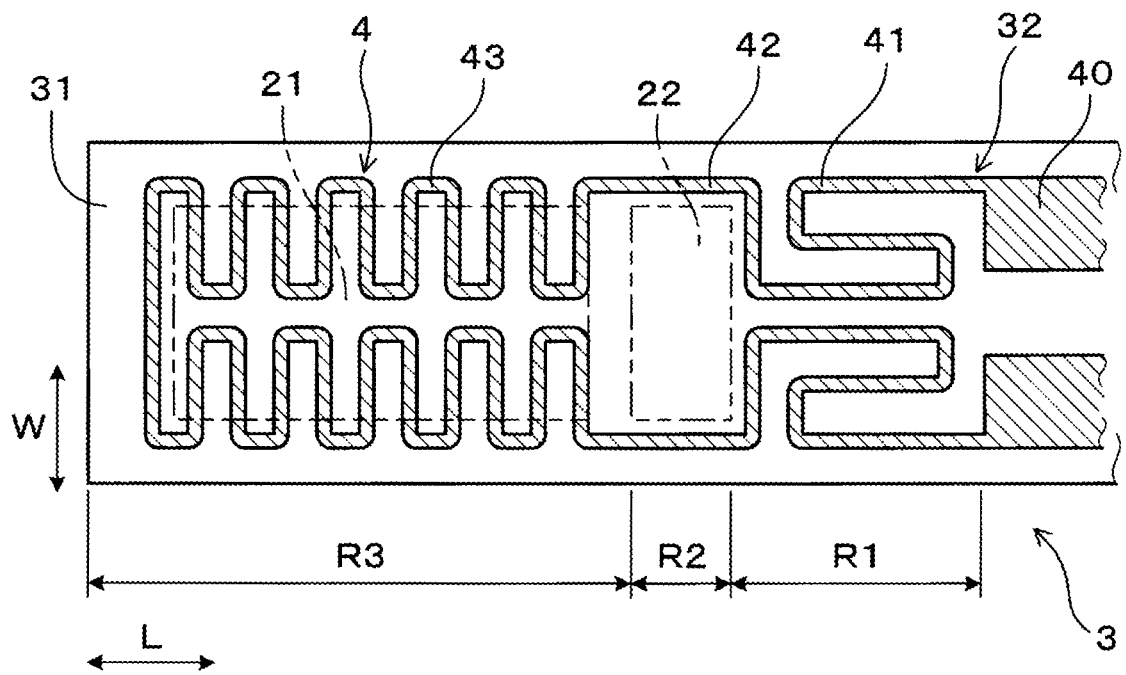
FIG. 6 is a plan view which illustrates the layout of a heating element in a heater base of another gas sensor according to the third embodiment.

The heating element 43 in the front end region R3 may be, as illustrated in FIG. 5, designed to include, like the heating element 41 in the base end region R1, portions extending parallel in the lengthwise direction L and portions extending parallel in the widthwise direction W. The portions extend continuously and meanders in the widthwise direction W. The heating element 42 in the intermediate region R2 lies outside ends of a region in the widthwise direction W which faces the sensor electrode 22 in the thickness-wise direction of the solid electrolyte body 2. The heating element 41 in the base end region R1, as illustrated in FIG. 6, may be designed to include portions extending parallel in the lengthwise direction L and portions extending parallel in the widthwise direction W and meander in the lengthwise direction L.

Figure 7:
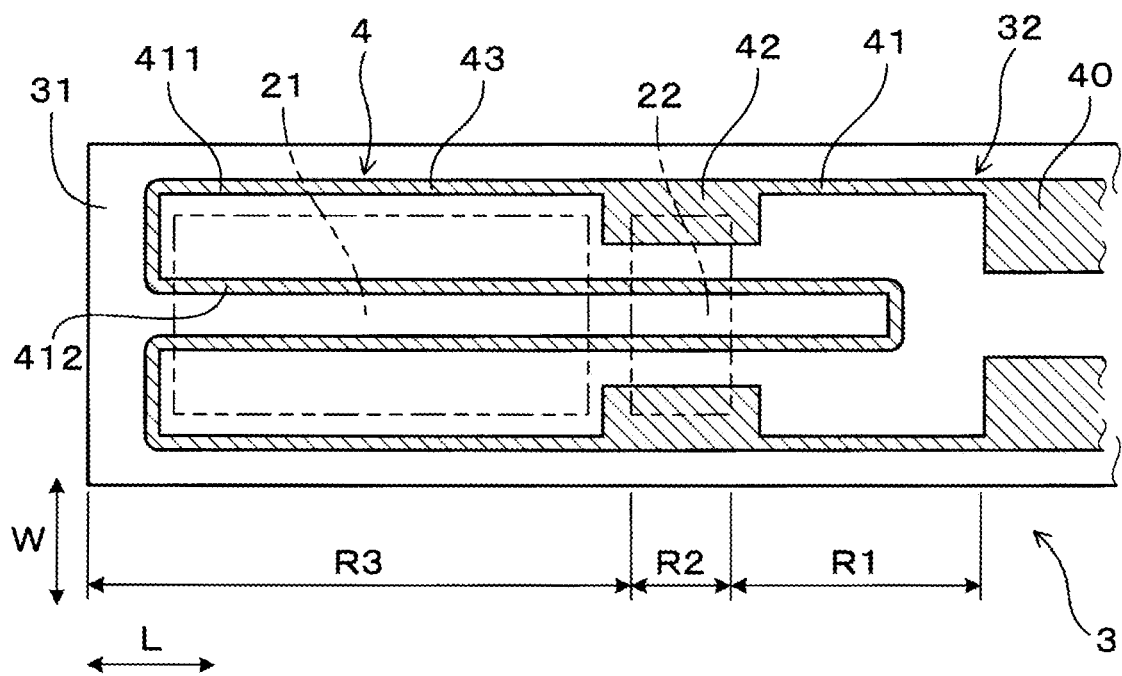
FIG. 7 is a plan view which illustrates the layout of a heating element in a heater base of another gas sensor according to the third embodiment.
Figure 8:
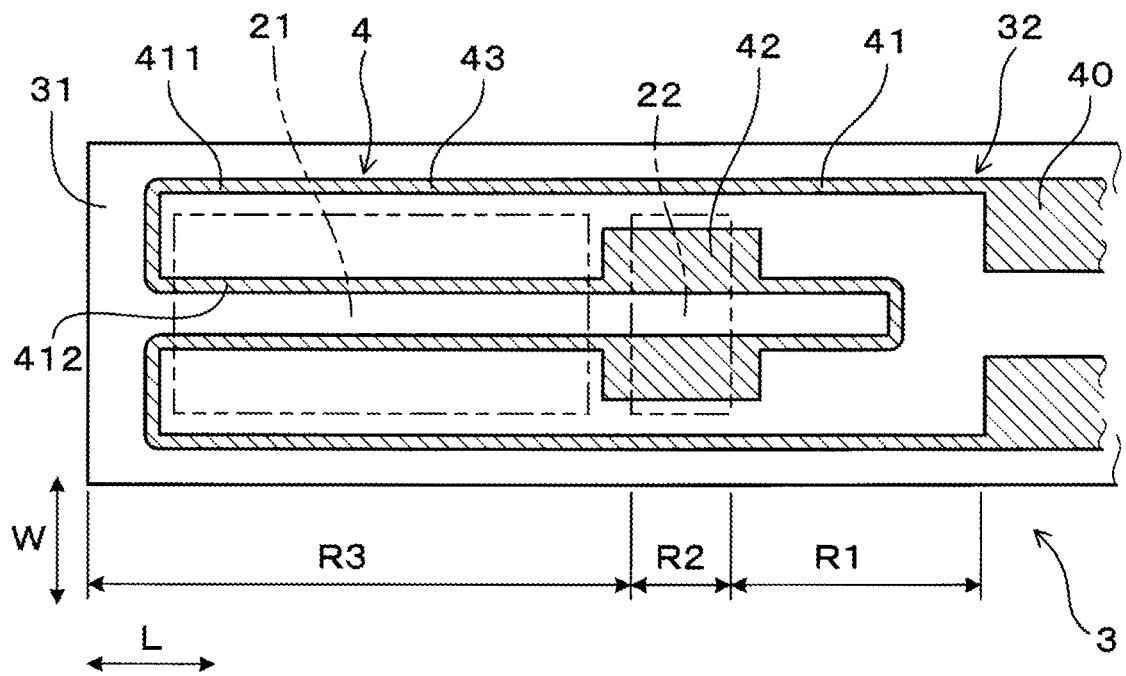
FIG. 8 is a plan view which illustrates the layout of a heating element in a heater base of another gas sensor according to the third embodiment.

The heating element 42 in the intermediate region R2 may, as illustrated in FIGS. 7 and 8, have at least a portion whose width is greater than that of the heating element 4 in the base end region R1 and the front end region R3. In this case, the heating element 4 may include two outer portions 411 and two inner portions 412 extending parallel in the lengthwise direction L over the whole of the base end region R1, the intermediate region R2, and the front end region R3 and meander in the lengthwise direction L. The two outer portions 411 lying in the intermediate region R2 may, as illustrated in FIG. 7, have a width greater than that of another portion of the heating element 4. The two inner portions 412 lying in the intermediate region R2 may alternatively be, as illustrated in FIG. 8, designed to have a width greater than that of another portion of the heating element 4.

In the cases in FIGS. 7 and 8, an average value of a sectional area per unit length of the heating element 41 lying in the base end region R1 and an average value of a sectional area per unit length of the heating element 43 lying in the front end region R3 are smaller than an average value of a sectional area per unit length of the heating element 42 disposed in the intermediate region R2. The average value of a sectional area per unit area, as referred to herein, is derived by dividing an average value of a transverse sectional area of each of the heating elements 41, 42, and 43 in the regions R1, R2, and R3 by an area of a corresponding one of the regions R1, R2, and R3.

This provides the resistance value per unit area of the heating element 41 in the base end region R1 and the resistance value per unit area of the heating element 43 in the front end region R3 which are greater than the resistance value per unit area of the heating element 42 in the intermediate region R2. This enables the amount of heat generated in the base end region R1 and the front end region R3 to be greater than that in the intermediate region R2.

The other arrangements of the gas sensor 1 of this embodiment are identical with those in the first embodiment. The same reference numbers as employed in the first embodiment will refer to the same parts. The same beneficial effects as those in the first embodiment are provided.

What is claimed is:

1. A gas sensor comprising:
a plate-like solid electrolyte body which has oxygen ion conductivity;
a pump electrode which is disposed on a first surface of the solid electrolyte body which is exposed to gas containing oxygen, the pump electrode being used to regulate an oxygen concentration in the gas;
a sensor electrode which is disposed closer to a base end side than the pump electrode is on the first surface of the solid electrolyte body, the sensor electrode being used to measure a concentration of a given gas component of the gas whose oxygen concentration has already been regulated by the pump electrode; and
a plate-like heater which is arranged to face the solid electrolyte body and works to heat the solid electrolyte body, wherein
the gas sensor has a front end side in a lengthwise direction thereof which is exposed to the gas and also has a base end side in the lengthwise direction which is retained by an insulator,
the heater is made up of a heater base and a conductive layer disposed in the heater base,
the conductive layer includes a pair of leads arranged on the base end side and a heating element, the heating element being arranged closer to the front end side than the leads are, connected to the leads, and smaller in sectional area than that of the leads, and
an entire region of a front end portion of the heater base in which the heating element is installed is broken down into three regions: a base end region, an intermediate region, and a front end region which are arranged in the above lengthwise direction, the intermediate region being located between a front end and a base end of the sensor electrode, the front end region being located closer to the front end side than the intermediate region is, the base end region being located closer to the base end side than the intermediate region is, resistance values per unit area of the heating element in the base end region and the front end region being higher than that in the intermediate region.

2. A gas sensor as set forth in claim 1, wherein a whole of the heating element has a constant sectional area, and a length per unit area of the heating element lying in the base end region and a length per unit area of the heating element lying in the front end region are greater than that of the heating element lying in the intermediate region.

3. A gas sensor as set forth in claim 1, wherein an average value of a sectional area per unit length of the heating element disposed in the base end region and an average value of a sectional area per unit length of the heating element disposed in the front end region are smaller than that of the heating element disposed in the intermediate region.

4. A gas sensor as set forth in claim 1, wherein the heating element lying in the base end region has portions extending parallel in the lengthwise direction and portions extending parallel in a widthwise direction perpendicular to the lengthwise direction and meanders in the widthwise direction.

5. A gas sensor as set forth in claim 1, wherein the heating element lying in the base end region has portions extending parallel in the lengthwise direction and portions extending parallel in a widthwise direction perpendicular to the lengthwise direction and meanders in the lengthwise direction.

6. A gas sensor as set forth in claim 4, wherein the heating element lying in the base end region is also formed in a central area located inside inner ends of the leads in the widthwise direction.

7. A gas sensor as set forth in claim 1, wherein the heater base has a portion which is opposed to the sensor electrode, and the heating element lying in the intermediate region is located outside ends of said portion of the heater base which are opposed to each other in the widthwise direction of the heater base.

8. A gas sensor as set forth in claim 1, wherein the heating element lying in the intermediate region includes a pair of outer portions extending in parallel in the lengthwise direction and a pair of inner portions extending in parallel in the lengthwise direction, the inner portions being located inside the outer portions in the widthwise direction.

9. A gas sensor as set forth in claim 7, wherein the heating element lying in the intermediate region has at least a portion whose width is greater than that of the heating element in the base end region and the front end region.

10. A gas sensor as set forth in claim 1, wherein the heating element lying in the front end region has portions extending parallel in the lengthwise direction and portions extending parallel in a widthwise direction perpendicular to the lengthwise direction and meanders in the lengthwise direction, and wherein the portions extending in the lengthwise direction includes a pair of outer portions and a pair of inner portions which are located inside the outer portions in the widthwise direction.

11. A gas sensor as set forth in claim 1, wherein the heating element lying in the front end region has portions extending parallel in the lengthwise direction and portions extending parallel in a widthwise direction perpendicular to the lengthwise direction and meanders in the widthwise direction.

12. A gas sensor as set forth in claim 1, wherein the heater base has a portion which overlaps with the sensor electrode in the thickness-wise direction of the heater base, and an outermost portion of the heating element lying in the intermediate region is located outside ends of said portion of the heater base which are opposed to each other in the widthwise direction of the heater base.

* * * * *